(12) United States Patent
Hallinan et al.

(10) Patent No.: US 8,586,789 B2
(45) Date of Patent: Nov. 19, 2013

(54) REMOVING HYDROCARBON IMPURITIES FROM ACETIC ACID PRODUCTION INTERMEDIATE

(75) Inventors: Noel Hallinan, Loveland, OH (US);
Brian A. Salisbury, Oxford, PA (US);
Shao-Hua Guo, Exton, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 348 days.

(21) Appl. No.: 12/383,896

(22) Filed: Mar. 30, 2009

(65) Prior Publication Data

US 2010/0249453 A1     Sep. 30, 2010

(51) Int. Cl.
*C07C 51/42*     (2006.01)

(52) U.S. Cl.
USPC .......................................... 562/608

(58) Field of Classification Search
None
See application file for complete search history.

(56) References Cited

U.S. PATENT DOCUMENTS

| | | | |
|---|---|---|---|
| 4,102,922 A * | 7/1978 | Price | 562/519 |
| 5,599,976 A * | 2/1997 | Scates et al. | 562/519 |
| 5,817,869 A | 10/1998 | Hinnenkamp et al. | |
| 5,932,764 A | 8/1999 | Morris et al. | |
| 7,790,919 B2 * | 9/2010 | Hallinan et al. | 562/519 |
| 2009/0281329 A1 | 11/2009 | Hallinan et al. | |

FOREIGN PATENT DOCUMENTS

| | | |
|---|---|---|
| EP | 0 686 619 A1 | 12/1995 |
| EP | 0686619  * | 12/1995 |
| GB | 343 947 A | 2/1931 |
| WO | WO 2009/114070 A1 | 9/2009 |
| WO | WO 2009/117055 A1 | 9/2009 |

OTHER PUBLICATIONS

Translation of claims 1-3 of EP 0686619 at http://www.wipo.int/patentscope/translate/translate.jsf (WIPO Patentscope).*
Translation of EP0686619.*

* cited by examiner

*Primary Examiner* — Karl J Puttlitz

(57) ABSTRACT

A method for removing hydrocarbon impurities from an acetic acid production intermediate is disclosed. The method comprises extracting the intermediate with a hydrocarbon extracting agent. The extraction is preferably performed with the alkane distillation bottom stream which comprises methyl iodide, acetic acid, and hydrocarbon impurities. The extraction forms a light phase which comprises the hydrocarbon impurity and the extracting agent and a heavy phase which comprises methyl iodide and acetic acid. The extraction heavy phase is optionally recycled to the alkane distillation or to the carbonylation reaction.

10 Claims, No Drawings

REMOVING HYDROCARBON IMPURITIES FROM ACETIC ACID PRODUCTION INTERMEDIATE

FIELD OF THE INVENTION

The invention relates to the preparation of acetic acid. More particularly, the invention relates to a method for removing hydrocarbon impurities from an acetic acid production intermediate.

BACKGROUND OF THE INVENTION

Acetic acid is commercially produced by methanol carbonylation. Prior to 1970, acetic acid was made using a cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem associated with the original Monsanto process is that a large amount of water (about 14%) is needed to produce hydrogen in the reactor via the water-gas shift reaction ($CO+H_2O \leftrightarrows CO_2+H_2$). Water and hydrogen are needed to react with precipitated Rh(III) and inactive [$Rh_4(CO)_2$] to regenerate the active Rh(I) catalyst. This large amount of water increases the amount of hydrogen iodide, which is highly corrosive and leads to engineering problems. Further, removing a large amount of water from the acetic acid product is costly.

In the late '70s, Celanese modified the carbonylation process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the early '90s, Millennium Petrochemicals developed a new rhodium carbonylation catalyst system that does not use iodide salt. The catalyst system uses a pentavalent Group VA oxide such as triphenylphosphine oxide as a catalyst stabilizer. The Millennium catalyst system not only reduces the amount of water needed but also increases the carbonylation rate and acetic acid yield. See U.S. Pat. No. 5,817,869.

One challenge still facing the industry is removing hydrocarbon impurities such as alkanes and aromatics from the methanol carbonylation. Methods for removing alkanes from acetic acid are known. For instance, U.S. Pat. No. 4,102,922 discloses an alkane removal method. According to the '922 patent, a slip stream from the heavy phase which comprises methyl iodide, acetic acid, water and alkanes is fed to an alkane distillation column with an overhead temperature of about 75° C. and a bottoms temperature of about 142° C. The bottoms temperature is run significantly higher than the overhead in order to minimize methyl iodide loss to the bottoms stream. The overhead of the alkane distillation, comprising mainly methyl iodide, is recycled to the reaction section. The bottoms stream comprising about 50% acetic acid and about 40% alkanes is removed from the system as waste. One problem associated with this method is that due to the high bottoms temperature, low boiling alkanes such as 2-methylpentane come with the overhead methyl iodide. This results in a build up of the low boiling alkanes in the reaction system as the overhead methyl iodide is recycled into the carbonylation reaction.

A new method for removing alkanes and other hydrocarbon impurities from the acetic acid production process is needed. Ideally, the method can effectively remove both high boiling and low boiling hydrocarbon impurities from the acetic acid production process.

SUMMARY OF THE INVENTION

The invention is a method for removing hydrocarbon impurities from an acetic acid production intermediate. The method comprises extracting the intermediate with a hydrocarbon extracting agent to form a light phase comprising the hydrocarbon impurity and the extracting agent and a heavy phase comprising acetic acid. Preferably, the extraction takes place with an alkane distillation bottoms stream which comprises methyl iodide, acetic acid and hydrocarbon impurities.

DETAILED DESCRIPTION OF THE INVENTION

Hydrocarbon impurities are produced by the side reactions of methanol carbonylation. Examples of hydrocarbon impurities include alkanes, alkenes, and aromatics. Alkane impurities commonly seen in the methanol carbonylation are $C_3$-$C_{12}$ alkanes including propane, butane, pentane, 2-methylbutane, 2,3-dimethylbutane, 2-methyl pentane, 3-methylpentane, hexane, octane, decane, cyclohexane, the like, and mixtures thereof. Commonly seen alkenes include propylene, butene, octene, the like, and mixtures thereof. Commonly seen aromatics include benzene, n-propylbenzene, toluene, xylene, the like, and mixtures thereof.

The carbonylation reaction is performed in the presence of a carbonylation catalyst and a catalyst stabilizer. Suitable carbonylation catalysts include those known in the acetic acid industry. Examples of suitable carbonylation catalysts include rhodium catalysts and iridium catalysts.

Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organorhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]RH(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds.

Most preferred co-catalysts are ruthenium compounds. Preferably, the co-catalysts are acetates.

Preferably, the reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is preferably performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is preferably performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydrolysis/methanolysis of polyvinyl acetate can be used for the carbonylation reaction.

The reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the reactor and then reacts with carbon monoxide and water to give acetic acid and regenerate hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

An acetic acid product stream is withdrawn from the reactor and is separated, by a flash separation, into a liquid fraction comprising the catalyst and the catalyst stabilizer and a vapor fraction comprising the acetic acid product, the reactants, water, methyl iodide, and impurities generated during the carbonylation reaction including alkanes, alkenes, and aromatics. The liquid fraction is recycled to the carbonylation reactor. The vapor fraction is then passed to a distillation column.

The distillation column, the so-called "light ends distillation," separates an overhead comprising methyl iodide, water, methanol, methyl acetate, and the hydrocarbon impurities from an acetic acid stream comprising acetic acid, a small amount of water, and some heavy impurities such as propionic acid. The acetic acid stream may be passed to a drying column to remove water and then be subjected to distillation, the so-called "heavy ends distillation," to remove the heavy impurities.

The overhead stream from the light ends distillation usually comprises from about 60 wt % to about 90 wt % of methyl iodide, from about 5 wt % to about 15 wt % of methyl acetate, from about 1 wt % to about 10 wt % of acetic acid, 1 wt % or less of water, from about 1 wt % to about 10 wt % of hydrocarbon impurities, and about 2 wt % or less of aldehyde impurities based on the total weight of the overhead.

The overhead stream is condensed and separated in a decanter to a light, aqueous phase and a heavy, organic phase. The heavy, organic phase comprises predominantly methyl iodide (greater than 50%) and the hydrocarbon impurities. The light, aqueous phase comprises predominantly water (greater than 50%), acetic acid, and methyl acetate. The aqueous phase is usually recycled to the reactor or to the light ends distillation.

At least a portion of the heavy, organic phase is distilled to form a vapor stream comprising the majority of methyl iodide (over 50% of the methyl iodide from the heavy organic phase) and a bottoms stream comprising the majority of acetic acid, methyl acetate, methyl iodide, and the hydrocarbon impurities (over 50% of each component from the heavy organic phase). This distillation is the so-called alkane distillation in the industry. The overhead temperature of the alkane distillation is preferably below about 75° C. so that there is no significant amount of hydrocarbon impurities coming out with the vapor stream. More preferably, the overhead temperature of the alkane distillation is within the range of about 43° C. (boiling point of methyl iodide) to about 75° C. Most preferably, the overhead temperature of the alkane distillation is within the range of about 43° C. to about 60° C. The particularly preferred overhead temperature of the alkane distillation is within the range of about 43° C. to about 45° C. The closer the overhead temperature of the alkane distillation to the boiling point of methyl iodide, the less the amount of hydrocarbon impurities existing in the vapor stream. The vapor stream is recycled to the carbonylation reaction. Lowering the overhead temperature of the alkane distillation, although reducing the hydrocarbon impurities in the vapor stream, results in a higher concentration of methyl iodide in the bottoms stream. According to current industrial practice, the bottoms stream is disposed as a waste. Thus, an increased amount of methyl iodide, an expensive material, is wasted.

The method of the invention comprises extracting the hydrocarbon impurities from any of the above intermediates or streams. Preferably the extraction is performed with the alkane distillation bottoms stream. The extraction is performed by mixing the alkane distillation bottoms stream with a hydrocarbon extracting agent and forming a light phase comprising the extracting agent and the hydrocarbon is impurities and a heavy phase which comprises methyl iodide and acetic acid. Preferably, the heavy phase contains less than 50% of the hydrocarbon impurities of the alkane distillation bottom stream. More preferably, the heavy phase contains essentially no hydrocarbon impurity. The heavy phase is optionally recycled to the alkane distillation or to the carbonylation reaction.

The hydrocarbon extracting agent is preferably selected from $C_9$ to $C_{20}$ aromatic or paraffinic hydrocarbons. Optionally, the extracting agent is a mixture of water with a $C_9$ to $C_{20}$ aromatic or paraffinic hydrocarbon. Water is used preferably in an amount of about 5% to about 50% by volume of the hydrocarbon extracting agent. The presence of water causes more acetic acid to go to the heavy phase which, as indicated above, can be recycled. The light phase is optionally disposed of or subjected to purification and recycling of the extracting agent.

Preferably, from about 5% to about 100% of the alkane distillation bottoms phase is subjected to the extraction. More preferably, from about 50% to about 100% of the alkane distillation bottom phase is subjected to the extraction.

Preferably, the ratio of the extracting agent to the alkane distillation bottom stream is in the range of 25/75 to 75/25 (V/V). The alkane distillation bottoms stream can be extracted more than once if desired.

The following examples are merely illustrative. Those skilled in the art will recognize many variations that are within the spirit of the invention and scope of the claims.

Example 1

Extraction of Alkane Distillation Bottoms Stream with Pentadecane

A simulated alkane distillation bottoms stream (5 parts by volume, containing 15.0 wt % of methyl iodide, 14.3 wt % of octane, and 70.7 wt % of acetic acid) is mixed with pentadecane (5 parts by volume) in a vial at room temperature (25° C.). A phase separation occurs. The ratio of light phase to heavy phase is 1.76 by weight. The light phase and the heavy phase are analyzed by ATR (attenuated total reflectance) infrared probe measurements. The light phase contains 12.9 wt % of octane, 4.1 wt % of methyl iodide, 17.3 wt % of acetic acid, and 65.7 wt % of pentadecane. The heavy phase contains 16.9 wt % of methyl iodide, 82.5 wt % of acetic acid, and <1 wt % of octane.

Example 2

Extraction of Alkane Distillation Bottoms Stream with Pentadecane

Example 1 is repeated but the volume ratio of pentadecane to the simulated alkanes distillation stream is 2.0. A phase separation occurs. The ratio of light phase to heavy phase is 4.11 by weight. The light phase contains 7.2 wt % of octane, 3.6 wt % of methyl iodide, 15.7 wt % of acetic acid, and 73.5 wt % of pentadecane. The heavy phase contains 16.5 wt % of methyl iodide, 82.7 wt % of acetic acid, and <1 wt % of octane.

Example 3

Extraction of Alkane Distillation Bottoms Stream with Pentadecane

Example 1 is repeated but the volume ratio of pentadecane to the simulated alkanes distillation stream is 3.0. A phase separation occurs. The ratio of light phase to heavy phase is 7.19 by weight. The light phase contains 5.1 wt % of octane, 2.2 wt % of methyl iodide, 14.7 wt % of acetic acid, and 78.0 wt % of pentadecane. The heavy phase contains 22.8 wt % of methyl iodide, 76.2 wt % of acetic acid, and <1 wt % of octane.

Example 4

Extraction of Alkane Distillation Bottoms Stream with Dodecane

A simulated alkane distillation bottoms stream (3 parts by volume, containing 17.5 wt % of methyl iodide, 5.9 wt % of decane, 6.8 wt % of hexane and 69.8 wt % of acetic acid) is mixed with dodecane (3 parts by volume) in a vial at room temperature (25° C.). A phase separation occurs. The ratio of light phase to heavy phase is 2.12 by weight. The light phase and the heavy phase are analyzed by infrared measurement. The light phase contains 3.8 wt % of decane, 4.3 wt % of hexane, 5.1 wt % of methyl iodide, 26.1 wt % of acetic acid, and 60.6 wt % of dodecane. The heavy phase contains 2.3 wt % of decane, 2.8 wt % of hexane, 21.1 wt % of methyl iodide, and 73.8 wt % of acetic acid.

Example 5

Extraction of Alkane Distillation Bottoms Stream with Pentadecane in the Presence of Water A simulated alkane distillation bottoms stream (5 parts by volume) of composition as described in Example 1 is mixed with pentadecane (13 parts by volume) and water (2 parts by volume) in a vial at room temperature (25° C.). A phase separation occurs. The ratio of light phase to heavy phase is 1.99 by weight. The light phase and the heavy phase are analyzed by infrared measurement. The light phase contains 3.3 wt % of octane, 6.4 wt % of methyl iodide, 4.7 wt % of acetic acid, and 85.6 wt % of pentadecane. The heavy phase contains 6.9 wt % of octane, 1.3 wt % of methyl iodide, 56.7 wt % of acetic acid, and 35.0 wt % of water.

Example 6

Extraction of Alkane Distillation Bottoms Stream with Pentadecane in the Presence of Water Example 5 is repeated but the simulated alkane distillation bottoms stream is mixed with pentadecane (10 parts by volume), and $H_2O$ (5 parts by volume) in a vial at room temperature. A phase separation occurs. The ratio of light phase to heavy phase is 1.04 by weight. The light and heavy phases are analyzed by infrared measurement. The light phase contains 6.2 wt % of octane, 8.2 wt % of methyl iodide, 1.0 wt % of acetic acid, and 84.6 wt % of pentadecane. The heavy phase contains 0.6 wt % of methyl iodide, 42.1 wt % of acetic, and 57.3 wt % of water.

We claim:
1. A method for removing impurities from an acetic acid production process comprising the steps of:
   removing a hydrocarbon impurity from an acetic acid production intermediate wherein the removing step further comprises the step of:
      extracting the acetic acid production intermediate with a hydrocarbon extracting agent to form:
         a light, aqueous phase comprising the hydrocarbon impurity and the extracting agent; and,
         a heavy, organic phase comprising acetic acid and methyl iodide, wherein the hydrocarbon extracting agent is a $C_{11}$ to $C_{20}$ aromatic or paraffinic hydrocarbon, and wherein the acetic acid production intermediate is an alkane distillation bottoms stream wherein the alkane distillation bottoms stream is composed of by weight a majority of acetic acid and the hydrocarbon impurity.

2. The method of claim 1, wherein the hydrocarbon impurity is selected from the group consisting of alkanes, alkenes, aromatics, and mixtures thereof.

3. The method of claim 2, wherein the alkane is a $C_3$-$C_{12}$ alkane.

4. The method of claim 1, wherein the intermediate comprises methyl iodide, acetic acid, methyl acetate and the hydrocarbon impurity.

5. The method of claim 1, comprising adding water to the extraction.

6. The method of claim 5 wherein the water is added to the extraction in an amount of 5% to 50% by volume of the hydrocarbon extracting agent.

7. The method of claim 1 wherein the ratio of the hydrocarbon extracting agent to the alkane distillation bottom stream is 25/75 to 75/25 (V/V).

8. The method of claim 1 wherein the hydrocarbon extracting agent is selected from the group consisting of pentadecane and dodecane.

9. The method of claim 1 wherein the heavy phase comprises greater than 15 wt % methyl iodide.

10. The method of claim 5 wherein the light phase comprises less than 5 wt % acetic acid.

* * * * *